United States Patent [19]
Boyles et al.

[11] Patent Number: 5,846,902
[45] Date of Patent: Dec. 8, 1998

[54] SAFENED SULFONAMIDE HERBICIDAL COMPOSITIONS

[75] Inventors: Mark C. Boyles, Ripley, Okla.; John M. Fenderson, Kiowa, Kans.; Bart Brinkman, Salem, Oreg.

[73] Assignee: Novartis Corporation, Summit, N.J.

[21] Appl. No.: 866,654

[22] Filed: May 30, 1997

Related U.S. Application Data

[63] Continuation of Ser. No. 351,863, Sep. 15, 1994, Pat. No. 5,739,080, which is a continuation-in-part of Ser. No. 207,103, Mar. 4, 1994, abandoned, which is a continuation of Ser. No. 68,727, May 26, 1993, abandoned.

[51] Int. Cl.$^6$ .................................................... A01N 25/32
[52] U.S. Cl. ............................................................ 504/110
[58] Field of Search .............................................. 504/110

[56] References Cited

U.S. PATENT DOCUMENTS

| | | | |
|---|---|---|---|
| 5,129,949 | 7/1992 | Cary et al. | 71/107 |
| 5,397,765 | 3/1995 | Cary | 504/110 |
| 5,614,466 | 3/1997 | Boyles et al. | 504/110 |

*Primary Examiner*—S. Mark Clardy
*Attorney, Agent, or Firm*—Lynn Marcus-Wyner; William A. Teoli, Jr.; John D. Peabody, III

[57] ABSTRACT

Co-application of auxin agonist herbicides such as dicamba and amino acid synthesis inhibitor herbicides such as ALS inhibitor herbicides (e.g., flumetsulan) reduces the incidence of phytotoxic effects, particularly in grassy crops.

9 Claims, No Drawings

SAFENED SULFONAMIDE HERBICIDAL COMPOSITIONS

This is a CONTINUATION of application Ser. No. 08/351.863, now U.S. Pat. No. 5,739,080, filed on Sep. 15, 1994 which is a CONTINUATION-IN-PART of application Ser. No. 08/207,103 filed on Mar. 4, 1994, abandoned, which is a CONTINUATION of application Ser. No. 08/068,727 filed on May 26, 1993 abandoned.

The present invention concerns a method of controlling undesired plant growth employing co-application of a growth regulator herbicide such as an auxin agonist herbicide and an amino acid synthesis inhibitor herbicide such as an ALS inhibitor herbicide.

Examples of auxin agonist herbicides include benzoic acids such as dicamba and phenoxy acids such as 2,4-D and MCPA.

The invention concerns in a preferred embodiment employing co-application of dicamba and an ALS inhibitor herbicide.

Examples of ALS inhibitor herbicides include sulfonylureas such as rimsulfaron (DPX 9636), metsulfuron, metsulfuron-methyl, ethametsulfuron, nicosulfuron, triasulfuron, primisulfuron, bensulfuron, chlorimuron, chorimuron-ethyl, chlorsulfuron, sulfometuron, thifensulfuron, tribenuron, triflusulfuron, clopyrasulfuron, and pyrazasulfuron; sulfonamides such as flumetsulan (DE498); and imidazolinones such as imazaquin, imazamethabenz, imazapyr, imazmethapyr and imazethapyr.

The above mentioned herbicides, processes for their production, herbicidal compositions containing them and their use as herbicides are known in the art and are described e.g. in the Pesticide Manual, 9th edition (1991), The British Crop protection Council, London and/or in Ag Chem New Product Review, Ag Chem Information Services, Indianapolis, Indiana and/or in Crop Protection Chemicals Reference, Chemical and Pharmaceutical Press (c/o John Wiley NY, NY) and/or in Farm Chemicals Handbook, Master Publishing Co., Willoughby, Ohio, each published annually or similar publications.

It has now surprisingly been found that co-application of a growth regulator herbicide, especially dicamba, and an amino acid synthesis inhibitor herbicide, especially an ALS inhibitor herbicide, results in a reduction of the phytotoxic effects of the latter particularly on grassy crops such as sorghum, corn and wheat without a corresponding reduction of effectiveness in the control of undesired plant growth.

The invention therefore concerns a method for reducing phytotoxicity to crop plants due to amino acid synthesis inhibitor herbicides, especially ALS-inhibitor herbicides which comprises co-applying to the crop or to the locus thereof a growth regulator herbicide such as an auxin agonist herbicide especially dicamba with said amino acids synthesis inhibitor herbicide.

Co-application can be achieved using tank mixes of preformulated individual active ingredients, simultaneous or sequential (preferably 1–2 days) application of such formulations or application of preformulated fixed pre-mix combinations of the individual active ingredients.

Auxin agonist herbicides, especially dicamba, are particularly suitable in the control of annual and perennial broadleaf weeds especially in post-emergent application and are selective in certain crops, especially corn and sorghum.

Amino acid synthesis inhibitors, especially ALS inhibitors, are active against a broad spectrum of both broadleaf and grassy weeds. Selectivity can be found in a wide range of individual crops depending upon the precise structure of the compound for example in the case of imidazolinones and sulfonylureas.

As mentioned above co-application according to the invention is particularly useful when employed for the control of weeds where ALS inhibitor herbicides such as sulfonylureas, sulfonamides and imidazolinones are employed in grassy crops such as sorghumn, corn and wheat. In such uses co-application according to the invention with auxin agonist herbicides, especially dicamba, reduces possible phytotoxic effects of the ALS inhibitors herbicides.

Preferred auxin agonists for use according to the invention are dicamba and 2,4-D, especially dicamba.

Preferred ALS inhibitors for use according to the invention are metsulfuron (-methyl), nicosulfuron, triasulfuron, primisulfuron, chlorimuron (-ethyl), chlorsulfuron, thifensulfuron, rimsulfuron, imazethapyr and imazmethapyr.

Particularly preferred combinations are thus dicamba with, for example, metsulfuron (-methyl), imazethapyr, triasulifuron, thifensulfuron, imazmethapyr, nicosulfuron, primisulfuron, rimsulfuron, chlorimuron (-ethyl), chlorsulfuron.

Examples of commercial forms of these preferred herbicides include dicamba—BANVEL®D herbicide
metsulfuron-methyl—ALLY® herbicide
imazethapyr—PURSUE® herbicide
triasulfuron—AMBER® herbicide
thifensulfuron—PINNACLE® herbicide
imazmethapyr—CADRE® herbicide
nicosulfuron—ACCENT® herbicide
prirnisulfuron—BEACON® herbicide
rimsulfuron—TITUS® herbicide
chlorimuron—CLASSIC® herbicide
chlorsulfuron—GLEAN® herbicide An example of a particular combination would be BANVEL® herbicide with ALLY® herbicide.

The application rates of the herbicides employed in co-application will of course depend on the active ingredients chosen, the weed to be controlled, the crop plant involved, soil type, season, climate, soil ecology and various other factors. Optimum usage is readily determinable by one skilled in the art using routine testing such as greenhouse or small plot testing. Application rates will usually be those recommended for use of commercially available forms of the active ingredients.

In general, for example, satisfactory results are obtained when co-applying at rates of 100 to 2000 gm/ha especially 250 to 1000 gm/ha of an auxin agonist herbicide, especially dicamba and 0.5 to 64 gm/ha eg. 2 to 64 gm/ha especially 1 to 30 gm/ha eg. 10 to 30 gm/ha of a(sulfonylurea herbicide or 100 to 3000, especially 150 to 1000 gm/ha of an imidazolinone herbicide.

In general, for example, the weight ratio of auxin agonist herbicide, especially dicamba, with a sulfonylurea lies conveniently within the range of from 50:1 to 500:1, especially 100:1 to 300:1.

Co-applied herbicides when formulated individually or as preformulated fixed pre-mixes are conveniently employed in association with agriculturally acceptable diluents or carriers.

Methods of preparing herbicidal formulations are described in the literature along with suitable liquid and solid carriers such as in U.S. Pat. No. 4,192,669 and 4,163,661 which are incorporated herein by reference.

A typical co-application of dicamba (a) with metsulfuron-methyl (x) would be e.g. from 50 to 500 gm/ha; especially 100 to 300 gm/ha of (a) and 0.5 to 10 gm/ha; especially 1 to 5 gm/ha of (x).

Details of weed spectra, selectivity, application rates and regimes and the like for individual active ingredients which may be employed according to the invention are also disclosed in the various references cited above.

Suitable formulations contain from 0.01 to 99% by weight of active ingredient(s), and from 1 to 99.99% of solid or liquid diluent(s) and other additives e.g. surfactants. Higher ratios of surfactant to active ingredient(s) are sometimes desirable and are achieved by incorporation into the formulation or at tank mixing. Application forms of a composition generally contain between 0.01 and 25% by weight of active ingredient(s). Lower or higher levels of active ingredient(s) can, of course, be present depending on the intended use, the physical properties of the compound and the mode of application. Concentrate forms of a composition intended to be diluted before use generally contain between 5 and 95%, preferably between 10 and 81% by weight of active ingredient(s).

Useful formulations of the active ingredients either alone or in combination include dusts, granules, suspension concentrates, wettable powders, flowables and the like. They are obtained in conventional manner, e.g. by mixing an active ingredient(s) each optionally as twin packs with the diluent(s) and optionally with other ingredients.

Alternatively, the active ingredients may be used in microencapsulated form.

Agriculturally acceptable additives may be employed in the herbicidal compositions to improve the performance of the active ingredient and to reduce foaming, caking and corrosion, for example. "Surfactant" as used herein means an agriculturally acceptable material which imparts emulsifiability, spreading, wetting, dispersibility or other surface-modifying properties. Examples of surfactants are lignin sulfonates, and fatty acid sulfonates, e.g. lauryl sulfonate, the condensation product of formaldehyde with naphthalene sulfonate, an alkylarylsulfonate, an ethoxylated alkylphenol, an ethoxylated fatty alcohol and the like. "Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms e.g. diesel oil or preferably water.

For co-application for example as tank mixes or in sequential treatment commercially available forms of the active ingredients may be employed.

The compositions of the invention can also comprise other compounds having biological activity, e.g. other compounds having a similar or complementary herbicidal or antidotal activity or compounds having fungicidal, insecticidal, or other pesticidal activity.

Solid forms for compositions are preferred from the point of view of environmentally innocuous packaging.

The following specific embodiments are considered within the purview of the invention.

A method for reducing phytotoxicity of amino acid synthesis inhibitor herbicides to crop plants, which comprises co-applying to the crop plants or to the locus thereof a phytotoxicity reduction effective amount of a growth regulator herbicide together with a herbicidally effective amount of said amino acids synthesis inhibitor herbicide (Embodiment A).

A method of selectively controlling unwanted plant growth in grassy crops which comprises co-application to the locus of said unwanted plant growth at least one amino acid synthesis inhibitor herbicide in an herbicidally effective amount and at least one growth regulator herbicide in a herbicidally and phytotoxicity reduction effective amount. (Embodiment B).

A method of controlling unwanted plant growth which comprises co-application to the locus of the said unwanted plant growth at least one growth regulator herbicide and at least one amino acid synthesis inhibitor herbicide in herbicidally effective aggregate amount. (Embodiment C).

A herbicidal composition comprising a herbicidally effective aggregate amount of a growth regulator herbicide and an amino acid synthesis inhibitor herbicide. (Embodiment D).

Preferred amino acid synthesis inhibitor herbicides for use according to embodiments A through D are ALS inhibitor herbicides (Embodiment E).

Preferred growth regulator herbicides for use according to embodiments A through D are auxin agonist herbicides (Embodiment F) with dicamba being particularly favored (Embodiment G).

Within Embodiment E the following ALS inhibitor herbicides are preferred; a sulfonylurea such as rimsulfuron, metsulfuron, metsulfuron-methyl, ethametsulfuron, nicosulfiaron, triasulfuron, primisulfuron, bensulfuron, chlorimuron, chiorimuron-ethyl, chlorsulfuron, sulfometuron, thifensulfuron, tribenuron, triflusulfuron, clopyrasulfuron or pyrazasulfuron, a sulfonamide such as flumetsulan or an imidazolinone such as imazaquin, imazamethabenz, imazapyr or imazethapyr or additionally imazmethapyr (Embodiment H).

Especially preferred ALS inhibitors within embodiment H are metsulfuron (-methyl), nicosulfuron, triasulfuron, primisulfuron, chlorimuron (-ethyl), S chlorsulfuron, thifensulfuron, rimsulfuron, or imazethapyr or additionally imazmethapyr. (Embodiment D).

When used in accordance with embodiments A through C the amount of auxin against herbicide is preferably from 50 to 2000 gm/ha eg 100 to 2000 gm/ha (Embodiment J).

When used in accordance with embodiments A through C the amount of amino acid synthesis inhibitor herbicide used in preferably from 0.5 to 64 gm/ha, eg 2 to 64 gm/ha of a sulfonylurea herbicide or from about 100 to 3000 gm/ha of an imidazolinone herbicide (Embodiment K).

Preferred herbicides for use in embodiments A through D include dicamba in combination with metsulfuron (-methyl) (Embodiment L).

The following examples illustrate the practice of the invention.

EXAMPLE 1

Field trials are conducted on five leaf sorghum to determine crop injury (=herbicide tolerance) and pigweed control. Products employed were ALLY® herbicide (metsulfuron-methyl; DuPont) in the commercially available 60% dry flowable form; BANVEL® herbicide (dicamba-DMA; Sandoz) in the 40% dicamba equivalent commercial form; 2,4-D (as 2,4-D-DMA 4SL=480 g a.i./L) and MARKSMAN® herbicide (dicamba-DMA+atrazine; Sandoz).

Application takes place post-emergent over the top when pigweed is 2" tall. Evaluations are carried out at from 1 to 8 weeks after treatment (WAT).

Results
SORGHUM:TOLERANCE - STUNT/PIGWEED CONTROL

| Product | Appl. Rate gm ai./ha | Sorghum Inj. % | Pigweed Cont. % |
|---|---|---|---|
| ALLY ® | 2.1 | 18 | 85 |
| ALLY ® 2,4-D | 2.1+ 280 | 13 | 94 |
| ALLY ® BANVEL ® | 2.1+ 280 | 7 | 92 |
| ALLY ® + MARKSMAN ® | 2.1+ 896 | 7 | 83 |
| ALLY ® | 1.05 | 13 | 76 |
| ALLY ® + 2,4-D | 1.05+ 280 | 4 | 93 |
| ALLY ® + BANVEL ® | 1.05+ 280 | 5 | 96 |
| ALLY ® + MARKSMAN ® | 1.05+ 896 | 3 | 75 |
| 2,4-D | 280 | 4 | 67 |
| BANVEL ® | 280 | 2 | 83 |
| MARKSMAN ® | 896 | 0 | 90 |

Application of ALLY® alone at both rates tested produces unacceptable stunt in sorgum. Co-application of ALLY® with 2,4-D, BANVEL® or MARKSMAN® reduces stunting without reducing weed control.

The optimum balance between reduced sorghum stunt and excellent pigweed control is shown by the combination of ALLY® and BANVEL® at both rates tested.

What is claimed is:

1. A herbicidal composition comprising a herbicidally effective aggregate amount of growth regulator herbicide and an amino acid synthesis inhibitor herbicide wherein the inhibitor herbicide is a sulfonamide and wherein the growth regulator herbicide reduces the phytotoxicity of said amino acid synthesis inhibitor herbicide to crop plants.

2. A composition according to claim 1 wherein the growth regulator herbicide is dicamba.

3. A composition according to claim 1 wherein growth regulator herbicide is dicamba and the amino acid synthesis inhibitor herbicide is flumetsulan.

4. A method for reducing phytotoxicity of amino acid synthesis inhibitor herbicides to crop plants, which comprises co-applying to the crop plant or to the locus thereof a phytotoxicity reduction effective amount of growth regulator herbicide together with a herbicidally effective amount of said amino acid synthesis inhibitor herbicide wherein the inhibitor herbicide is a sulfonamide.

5. A method according to claim 4 wherein the growth regulator herbicide is dicamba.

6. A method according to claim 4 wherein the growth regulator herbicide is dicamba and the amino acid synthesis inhibitor herbicide is flumetsulan.

7. A method of selectively controlling unwanted plant growth in grassy crops with comprise co-applying to the locus of said unwanted plant growth at least one amino acid synthesis inhibitor herbicide in an herbicidally effective amount and at least one growth regulator herbicide in a herbicidally and phytotoxicity reduction effective amount wherein the inhibitor herbicide is a sulfonamide.

8. A method according to claim 7 wherein the growth regulator herbicide is dicamba.

9. A method according to claim 7 wherein the growth regulator herbicide is dicamba and the amino acid synthesis inhibitor herbicide is flumetsulan.

* * * * *